United States Patent [19]

Strauss et al.

[11] Patent Number: 5,200,178
[45] Date of Patent: Apr. 6, 1993

[54] METHOD FOR TUMOR DETECTION

[75] Inventors: H. William Strauss, Newton Center; Robert H. Rubin, Brookline; Ban An Khaw, Milton; Faina Shtern, Boston, all of Mass.

[73] Assignee: The General Hospital Corporation, Boston, Mass.

[21] Appl. No.: 731,384

[22] Filed: Jul. 16, 1991

Related U.S. Application Data

[63] Continuation of Ser. No. 161,040, Feb. 26, 1988, abandoned.

[51] Int. Cl.$^5$ ............... A61K 49/02; A61K 49/00
[52] U.S. Cl. ............................ 424/1.1; 424/9; 424/85.8; 514/2; 530/391.3; 436/173
[58] Field of Search ................ 424/1.1, 9, 85.8; 514/2; 530/391.3; 436/173

[56] References Cited

U.S. PATENT DOCUMENTS

| | | |
|---|---|---|
| 4,331,647 | 5/1982 | Goldenberg ............... 424/9 |
| 4,444,744 | 4/1984 | Goldenberg . |
| 4,472,509 | 9/1984 | Gansow et al. . |
| 4,636,380 | 1/1987 | Wong . |

OTHER PUBLICATIONS

Kerbel et al., *Cell*, vol. 3, pp. 105–112 (Oct. 1974).
Ran et al., *Chemical Abstracts*, vol. 110(3), 22030b, 1989.
Sunaga et al., *Chemical Abstracts*, vol. 101(13), 108241x (Sep. 1984).
Schirrmacher et al., *Journal of Supramolecular Structure* 11:105–115 (1979).
Zalcberg, J. R., *Am. J. Clin. Oncol.* 8:481–489 (1985).
Carrasquillo, J. A., et al., *Canc. Treat. Rpts.* 68:317–328 (1984).
Khaw, B. A., et al., *J. Nucl. Med.* 25:592–603 (1984).
Nelp, W. B., et al., *J. Nucl. Med.* 28:34–41 (1987).
Hayes, D. F., et al., *Canc. Res.* 46:3157–3163 (1986).
Murray, J. L., et al., *J. Nucl. Med.* 28:25–33 (1987).
Larson, S. M., *J. Nucl. Med.* 26:538–545 (1985).
Hwang, K. M., et al., *J. Natl. Canc. Inst.* 76:849–855 (1986).
Shtern, F., et al., *J. Nucl. Med.* 28:572–573 (1987).
Harwood, P. J., et al., *Eur. J. Canc. Clin. Oncol.* 21:1515–1522 (1985) (Note p. 1518 does not exist).
Siden, E., et al., *J. Immunol. Meth.* 87:251–255 (1986).
Svennevig et al., *Br. J. Cancer* 45:201–208 (1982).
Titus et al., *Proc. Natl. Acad. Sci. USA* 78(1):519–523 (1981).
Shen et al., *Proc. Natl. Acad. Sci. USA* 81:1445–1447 (1984).
Wright et al., *JNCI* 78(6):1061–1068 (1987).

*Primary Examiner*—Robert L. Stoll
*Assistant Examiner*—C. Sayala
*Attorney, Agent, or Firm*—Sterne, Kessler, Goldstein & Fox

[57] ABSTRACT

The invention relates to a method of detecting an Fc receptor-expressing tumor site in an individual by administering to the individual a diagnostically effective amount of detectably-labeled non-specific immunoglobulin or Fc or Fc' fragment thereof, wherein the immunoprotein substantially accumulates at the site when the site bears such a tumor. By using a therapeutically-labeled specific or non-specific immunoglobulin or Fc or Fc' fragment thereof, the tumor may be treated therapeutically.

13 Claims, No Drawings

METHOD FOR TUMOR DETECTION

This application is a continuation of application Ser. No. 07/161,040, filed Jan. 26, 1988, now abandoned.

BACKGROUND OF THE INVENTION

1. Field of the Invention

This invention is directed to a method of diagnosing a tumor site in an individual by a non-invasive technique, and treating such tumor by a similar non-invasive technique.

2. Description of the Background Art

Currently available non-invasive diagnostic methods of tumor localization include isotope scans (e.g. liver scan, gallium scan), radiology (e.g. plain X-ray, barium meal, computerized tomography), and ultrasonography. Such methods vary in their sensitivity, depending upon the size, site, and histological type of cancer, but all of them are nonspecific. Zalcberg, J. R., Am. J. Clin. Oncol. 8:481-9 (1985).

Antibodies have long been recognized as potential target-specific imaging agents. Pressman et al. (J. Immunol. 59:141-6 (1948)) were the first to demonstrate conclusively the localization of radiolabeled antibodies in specific target organs in vivo. Since then, antibodies have been used for detection and visualization of various malignant tissues in experimental animals. (For a review, see Zalcberg, supra. and Carrasquillo, J. A., et al., Cancer Treatment Reports 68:317-28 (1984).)

Early studies used the immunoglobulin fractions of tumor-specific antisera for detection of tumors, or non-specific markers such as anti-fibrinogen, usually detectably labeled with radioactive $^{131}$I. More recently, antibodies to oncofetal proteins, also labeled with $^{131}$I, were used as immunologic tumor imaging agents; however, the amount of radiolabeled antibody localized in the tumor was low compared with that localized in the blood and other organs, particularly the liver, thus limiting the clinical utility of such methods.

Advances in the production of tumor-specific or tumor-associated antibodies led to the advent of monoclonal antibody technology to provide a source of large quantities of a specific antibody directed against a single epitope. Kohler, G., et al., Nature 256:495-7 (1975); Mach, J. R., et al., Immunol. Today 2:239-49 (1981).

Improvements in radiolabeling now permit the formation of stable, pharmacologically inert complexes of antibody with isotopes such as technitium-99m or indium-111. These radiolabels, which have desirably short half-lives, allow high quality images to be recorded by scintigraphy with low radiation burden to the patient. Khaw, B. A., et al., J. Nucl. Med. 25:592-603 (1984).

Radiolabels have generally been attached to antibody proteins by two general techniques: oxidation methods and coupling with cross-linkers. Oxidation methods include chloramine-T, lactoperoxidase, and chloramide iodogen (see, for example: Zalutzsky, M., et al., Int. J. Nucl. Med. Biol. 12:227-33 (1985); Sternthal, E., et al., New Engl. J. Med. 303:1083-8 (1980); and Marchalonis, J. J., et al., Biochem. J. 113:299-205 (1969)). Coupling of radiolabels to antibody proteins using cross-linkers such as diethylenetriaminepentacetic acid cyclic anhydride in the presence of $SnCl_2$ and citrate in the presence of $SnCl_2$ are the current methods of choice. (See, for example, Krejcarek, G. E., et al., Biochem. Biophys. Res. Commun. 77:581-5 (1977); Khaw, B. A., et al., Science 209:205-7 (1980); Khaw, B. A., et al., J. Nucl. Med. 23:1011-19 (1982); Wong, D. W., U.S. Pat. No. 4,636,380; and Gansow, O. A., et al., U.S. Pat. No. 4,472,509.) Generally such labeling procedures produce a labeled immunoprotein which retains its physicobiological properties, is pharmacologically inert, and is suitable for imaging tumors.

Wong, U.S. patent supra, has disclosed the use of indium-111-labeled, tumor-specific autologous polyclonal antibodies for tumor imaging by scintigraphy. $^{111}$In-labeled human fibrinogen was also disclosed by this patent for neoplasm imaging.

Detectably labeled monoclonal antibodies directed to specific tumor antigens have achieved prominence in imaging specific tumors in vivo by scintigraphy (see, for example, Carrasquillo, supra; Khaw, supra: Zalcberg, supra; Nelp, W. B., et al., J. Nucl. Med. 28:34-41 (1987); Hayes, D. F., et al., Cancer Res. 46:3157-63 (1986); Murray, J. L., et al., J. Nucl. Med. 28:28-33 (1987); Larson, S. M., J. Nucl. Med. 26:538-45 (1985); Hwang, K. M., et al., J. Natl. Canc. Inst. 76:849-55 (1986); Goldenberg, M. D., U.S. Pat. No. 4,624,846; and Wong, D. W., U.S. Pat., supra).

Anti-tumor monoclonal antibodies (TMoAb) are directed against antigenic determinants that are selectively expressed on the surfaces of tumor cells. However, before such monoclonal antibodies can be used for imaging purposes, two essential criteria must be fulfilled. Hwang, supra. The first criterion is the target antigen specificity of the individual tumor monoclonal antibody. This is established by preliminary experiments on both tissue sections and cultured cells using a variety of techniques to establish both surface and intracellular antigen expression. A second criterion, which also requires examination in a systematic manner, is the pharmacokinetics of the putative TMoAb; this involves a comparison of the uptake by tumor relative to that by normal tissue, determination of the extent of degradation of the antibody to inert species by the host's enzymes, and excretion of the antibody or fragments thereof by the kidney.

The preparation of a specific TMoAb that meets all necessary criteria for tumor imaging is a difficult, laborious and expensive process. Larson, supra. The overall procedure entails: (1) isolation and identification of the specific tumor antigen; (2) immunizing a mouse against this antigen; (3) preparing spleen cells from such an immunized mouse and fusing these cells with an immortal human cell line (e.g. myeloma cells); (4) establishing hybridoma colonies; (5) identifying hybridomas that secrete the antibody of interest, particularly those that produce large quantities; (6) cloning the hybridomas of interest; (7) isolating and purifying all of the different monoclonal antibodies; and (8) determining whether single or multiple TMoAb's are required for tumor imaging, as each monoclonal antibody is directed to a specific epitope on the tumor antigen.

Another complication in the use of TMoAb arises from its frequently inadequate concentration at tumor sites, and from its tendency to form immune complexes that are poorly excreted by the kidney. This, in turn, has created a need to use fragments derived from the monoclonal antibody for tumor imaging. It has been reported that antibody fragments such as F(ab')$_2$ or Fab, perhaps because of their relatively small size, diffuse more easily into tumors and are excreted more rapidly by the kidney. Thus, the tumor to blood ratio might be increased as a result of these two concurrent events. Zalcberg, supra at 484; Mach et al., supra: Larson et al., supra;

Khaw et al., supra; Carrasquillo et al., supra. The F(ab')2 and Fab fragments of the immunoglobulin IgG represent the specific, variable N-terminal heavy and light chain domains of the immunoglobulin. These fragments must be prepared from the parent protein by proteolysis with specific proteinases, followed by isolation and rigorous purification.

Immunoglobulin molecules can bind to the surfaces of tumor cells by two mechanisms. The first requires the presence of a specific antigenic determinant on the cell surface, which interacts with an immunological site found in the variable region of the antibody. This region contains the tumor-specific F(ab)2 and Fab fragments previously used in tumor imaging (see supra). The second mechanism requires a cell-surface receptor that binds to a non-specific constant (Fc) region of homologous and heterologous immunoglobulins. Such receptors are termed the Fc receptors. Various cells of the reticuloendothelial and lymphatic tissues (monocytes, macrophages, T and B lymphocytes), as well as malignancies from these cells (such as lymphoma, sarcomas, and leukemias), as well as certain types of breast and lung cancer, possess Fc receptors on their surfaces. The amino acid sequence of the heavy chain C-terminal domain of the immunoglobulin (Fc) fragment remains relatively stable, regardless of the antigenic stimulus.

Thus, there is a distinct difference between the preparation of an antibody that is capable of reacting specifically via its Fab region with a particular tumor-specific epitope, and a non-specific immunoglobulin that interacts with the Fc receptor on cells at the tumor site. A tumor imaging approach that can employ the latter mechanism would be highly desirable because of its simplicity and inexpensive nature.

SUMMARY OF THE INVENTION

The present invention relates to a substantially non-invasive method of diagnosing sites of certain tumors in patients and of treating such tumors.

The present inventors have discovered that, when an intact human immunoglobulin is allowed to contact both a normal and a tumor site expressing Fc receptors in an individual, the intact immunoglobulin tends to accumulate at the tumor site.

Further, it was surprisingly discovered that the accumulation of immunoglobulin at the site of the Fc receptor-bearing tumor is not dependent upon the epitopic specificity of the immunoglobulins, and that non-specific immunoglobulins and the Fc, but not F(ab')2, portions of the immunoglobulin will accumulate at the site of the tumor.

This effect, the concentration of polyclonal immunoglobulin and the Fc fragment derived therefrom at tumor sites expressing Fc receptors, but no concentration of the F(ab')2 fragment derived therefrom, and the use of this property in non-invasive diagnostic imaging and therapeutic treatment of such tumors, has not been previously recognized. In other words, non-specific immunoglobulins or mixtures thereof, or non-specific Fc fragments derived therefrom can be used for imaging of Fc receptor-expressing tumors.

The present invention thus relates to an in vivo method of detecting an Fc receptor-expressing tumor site in an individual, this method comprising administering to the individual a detectably labeled non-specific immunoglobulin or Fc fragment obtained therefrom, wherein the immunoprotein substantially accumulates at the tumor site when the site expresses Fc receptors.

DESCRIPTION OF THE PREFERRED EMBODIMENTS

The invention relates to a method of detecting a tumor site in vivo in an individual which comprises administering to such an individual a diagnostically effective amount of a detectably labeled immunoglobulin or an Fc fragment thereof, wherein such immunoprotein substantially accumulates at such a tumor site when the site is an Fc receptor-bearing tumor. The invention also relates to an antibody-based method of treating such Fc receptor-bearing tumors.

By the term "individual" is meant to include both animals and humans.

By the term "tumor" is intended abnormal growth of cells that may result in the invasion of normal tissue sites or in the spread through distant organs. Tumors may be malignant or benign. By the term "malignant" is intended those abnormal cells that exhibit the propensity for invasion and distant spread. By "benign" is intended those abnormal cell growths that are not invasive in character.

By the term "Fc receptor-expressing tumor" is intended those tumors, particularly of hematopoietic or reticuloendothelial cell origin, that produce and insert into their cell surfaces special proteins termed "Fc receptors," that recognize and bind with high affinity to the non-specific, constant heavy chain portion of circulating immunoglobulins, termed "Fc region" or "Fc fragment." Examples of cell types that express large numbers of Fc receptors include monoclonal phagocytes, granulocytes, lymphocytes, basophils, and mast cells. Examples of tumors of such cell types include melanomas, lymphomas, sarcomas, leukemias, as well as certain types of breast and lung cancer.

By the term "non-specific immunoglobulin or Fc or Fc' fragment thereof" is intended any intact non-specific immunoglobulin or Fc or Fc' fragment thereof, whether monoclonally or polyclonally derived, that has no epitopic specificity for the tumor site and that can be directed against any antigen, including tumor binding sites necessary to effect binding of said non-specific immunoglobulin or Fc or Fc' fragment thereof to tumors and to accumulate at the site thereof.

Polyclonal immunoglobulin preparations can be derived directly from the blood of the desired animal species. Thus, in the case of humans, polyclonal immunoglobulin preparations can be prepared from outdated units of blood utilizing protocols known or readily ascertainable to those of ordinary skill in the art. Such products are commercially available (Sandoz Limited; Cutter Laboratories; Hyland Laboratories) and are conventionally used in the treatment of immunodeficiency states, but not in diagnosis.

In addition, if desired, polyclonal immunoglobulin preparations may be prepared from the blood of immunized individuals of the desired species following immunization with any of a variety of antigens, followed by harvesting of the blood and processing it according to defined techniques. A distinctive advantage of non-specific, immunoglobulin preparations is that by preparing immunoglobulin from the same species into which it will be injected, immune reactions across species barriers are prevented and repeated injections of the same product are less likely to cause side-effects. It should be emphasized that cross-species injections can be done. However, their use might increase the incidence of untoward reactions such as anaphylactic reactions, febrile reactions, and/or the generation of an immune response to the foreign immunoglobulin protein that will block its effective use, as well as endanger the health of the patient. The avoidance of such reactions adds greatly to the appeal of using an immunoglobulin preparation which is from the same species as that being diagnosed.

Monoclonal immunoglobulins which can be used according to the method of the invention can be prepared using hybridoma fusion techniques (Kohler et al., European Journal of Immunology 6:292, 1976) or can be derived from known secreting myeloma cell lines such as those available from depositories such as the American Type Culture Collection. As with the polyclonal immunoglobulin preparation, no antigenic or epitopic specificity is needed for the monoclonal immunoglobulin preparation to function effectively in this method. As a consequence, monoclonal antibodies of any specificity can be used.

In detecting an in vivo Fc receptor-expressing tumor site in an individual, the detectably labeled immunoglobulin is advantageously given in a dose which is diagnostically effective. The term "diagnostically effective" means that the amount of detectably labeled immunoglobulin administered is sufficient to enable detection of the tumor site when compared to the background signal. It is preferred that the non-specific immunoglobulin exhibit no non-tumor binding. However, to the extent that non-tumor binding of the immunoglobulin does occur, one with ordinary skill will be able to differentiate over tumor-bound immunoglobulin based on location, intensity of the image, and the like.

Generally, the dosage of detectably labeled immunoglobulin for diagnosis will vary depending on considerations such as age, condition, sex, and extent of disease in the patient, counterindications, if any, and other variables, to be adjusted by the individual physician. Dosage can vary from 0.0003 mg/kg to 0.3 mg/kg.

The term "Fc fragment or part thereof" as used in this invention is meant to include intact Fc fragments as well as portions of the Fc fragment capable of accumulating at the site of the tumor. Fc fragments, which contain the $C_H1$, $C_H2$ and $C_H3$ domains of the IgG molecule, are produced by proteolytic methods (i.e., use of the proteinase papain) well known to those of ordinary skill in the art. A fragment of the Fc domain, termed "Fc'," consists of the separated C-terminal $C_H3$ domain of the IgG molecule. By the term "Fc' fragment" as used herein is intended a detectably-labeled $C_H3$ fragment of the IgG molecule that is capable of substantially accumulating at a tumor site. Fc' fragments are prepared by a combination of proteinases, employed sequentially, namely, papain, pepsin and subtilisin.

The term "detectably labeled" means that the immunoglobulin has attached to it a diagnostically detectable label.

There are many different labels and methods of labeling known to those of ordinary skill in the art. Examples of the types of labels which can be used in the present invention include radioactive isotopes and paramagnetic isotopes. Those of ordinary skill in the art will know of other suitable labels for binding to the immunoglobulins used in the invention, or will be able to ascertain such, using routine experimentation. Furthermore, the binding of these labels to the immunoglobulin can be done using standard techniques common to those of ordinary skill in the art.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140–200 keV range, which may be readily detected by conventional gamma cameras.

For in vivo diagnosis, radionuclides may be bound to immunoglobulin either directly or indirectly by using an intermediary functional group. Intermediary functional groups which are often used to bind radioisotopes which exist as metallic ions to immunoglobulins are diethylenetriaminepentaacetic acid (DTPA) and ethylenediaminetetracetic acid (EDTA). Typical examples of metallic ions which can be bound to immunoglobulins are $^{99m}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

The immunoglobulins used in the method of the invention can also be labeled with paramagnetic isotopes for purposes of in vivo diagnosis. Elements which are particularly useful (as in Magnetic Resonance Imaging (MRI) techniques) in this manner include $^{157}Gd$, $^{55}Mn$, $^{162}Dy$, $^{52}Cr$, and $^{56}Fe$.

Alternatively, the method of the invention can be used to monitor the course of tumor invasiveness or metastasis in an individual. Thus, by measuring the increase or decrease in the size or number of tumor sites by serial imaging it would be possible to determine whether a particular therapeutic regimen aimed at ameliorating the cause of the tumorigenic process, or the tumor itself, is effective.

Another embodiment of the invention includes a method for tumor therapy wherein the non-specific immunoglobulin or Fc fragment therefrom of the invention is modified, prior to administration to an individual, by coupling to it covalently a cytotoxic material such as the lectin ricin which has a cell-destructive capability. Thus, the ricin, delivered by the immunoproteins of the invention, will destroy the tumor cells, when delivered in therapeutically effective concentrations.

The invention also embodies another method for tumor therapy. In this method, an individual suspected of having an Fc receptor-bearing tumor site is first administered a diagnostically effective amount of non-specific immunoglobulin or Fc fragment thereof, as previously described. This detectably labeled immunoprotein may be of the same or different species as the individual to whom it is being administered. The individual suspected of having a tumor site is then imaged to determine the presence of such a site. If the individual is found to have a tumor site, the individual is then given an antibody preparation(s) specific for the tumor which is suspected. This specific antibody can be from an individual of the same, or a different, species to that of the individual having the tumor site. After determining the specific tumor type it is then possible to administer a therapeutic agent, such as therapeutically conjugated antibody specific for the tumor or tumorigenic tissue at the tumor site. By "treating" is intended the administration to an individual of an agent that has an ameliorative, curative or prophylactic effect upon the tumor or tumorigenesis.

The term "therapeutically conjugated" means that a non-specific or specific immunoglobulin or fragment thereof used in the just-described preferred method of the invention is conjugated to a therapeutic agent. The therapeutic agents used in this conjugate act directly upon the tumor or upon the underlying cause of the tumor site. Examples of therapeutic agents that can be coupled to the specific antibodies used according to the method of the invention are anti-tumor drugs, DNA alkylating agents, analogs of nucleotides and nucleosides, DNA intercalcating drugs, antimetabolites, radioisotopes, lectins, toxins, and antibiotics. Many antitumor chemicals are known in the art. A requirement of the present invention is that the therapeutic means should not be conjugated to the Fc portion of the immunoglobulin so as not to block binding of the therapeutic immunoprotein to the Fc receptor-bearing tumor.

By the term "lectins" is intended a glycoprotein, usually isolated from plant material, which bind to specific sugar moieties. Many lectins are also able to agglutinate cells and stimulate lymphocytes. Certain lectins are extremely toxic to animal cells. For example, ricin is a toxic lectin which has been used immunotherapeutically. This is accomplished by binding the alpha-peptide chain of ricin, which is responsible for toxicity, to the antibody molecule to enable sitespecific delivery of the toxic effect.

Toxins are poisonous substances produced by plants, animals, or microorganisms that, in sufficient dose, are often lethal. One such toxin is diphtheria toxin, a protein produced by *Corynebacterium diohtheriae* that inhibits protein synthesis in various cell types. This toxin consists of an alpha and beta subunit which, under proper conditions, can be separated. The toxic component can be bound to antibody and used for site-specific delivery to the primary or metastisizing tumor sites.

Examples of radioisotopes which can be bound to specific antibody for therapeutic purposes, used according to the method of the invention, are $^{125}I$, $^{131}I$, $^{90}Y$, $^{67}Cu$, $^{217}Bi$, $^{211}At$, $^{212}Pb$, $^{47}Sc$, $^{109}Pd$, and $^{184}Re$.

Antibiotics are substances which inhibit such infectious microorganisms as bacteria, viruses, fungi, and parasites. These antibiotics can be any of those known to those of ordinary skill in the art.

Other therapeutic agents which can be coupled to immunoproteins used according to the method of the invention are known, or can be easily ascertained, by those of ordinary skill in the art.

Preparations of the imaging immunoglobulins for parenteral administration include sterile aqueous or non-aqueous solutions, suspensions, and emulsions. Examples of non-aqueous solvents are propylene glycol, polyethylene glycol, vegetable oil such as olive oil, and injectable organic esters such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, and inert gases and the like.

See, generally, *Reminoton's Pharmaceutical Science*, 16th ed., A. Osol, ed., Mack, 1980.

The above disclosure generally describes the present invention. A more complete understanding can be obtained by reference to the following specific example which is provided herein for purposes of illustration only, and is not intended to be limiting unless otherwise specified.

EXAMPLE 1

Murine ovarian reticulum cell sarcoma of monocytic origin (M5076), an Fc receptor-bearing tumor, was implanted intramuscularly in the right thigh of syngeneic C57BL/6 in-bred mice. Five days post-implantation of a 10 mg tumor, each mouse was injected with 40-50 ug (60-80 uCi) of one of the following $^{111}$In-labeled types of antibodies: intact polyclonal human IgG, or its purified Fc or F(ab')2 fragment. $^{111}$InCl was coupled to immunoproteins by the mixed and cyclic anhydride-DTPA methods, as described, for example, by B. Khaw et al., *Science* 209:295 (1980) and Hnatowich et al., *Jour. of Appl. Radiat. Isot.* 33:327 (1982). At least 6 mice per group were used. Scintigraphic imaging was performed on a gamma camera with pinhole collimation immediately post-injection of the radiolabeled material, and again at 24 and 48 hours thereafter. The animals were imaged for ten minutes each. Whole body, organ, and tumor uptake of the radiopharmaceuticals was calculated according to the following formula: (organ counts-background counts/standard counts) * (standard dose/injected dose). Biodistribution of radiolabel in tissues (Table 1 infra) was done at 48 hours. At the time of sacrifice, tumor size was about 20 mg.

In order to compare tumor uptake of Fc to that of Fab, $^{111}$In-labeled antibody modified by cyclic DTPA was used, and one group of mice received radiolabeled Fc fragments and the second group radiolabeled Fab fragments.

In order to compare tumor localization with $^{125}$I-labeled antibody to that of $^{111}$In-labeled antibody, six animals were injected with doubly-labeled intact polyclonal IgG, and both $^{111}$In and 25I peaks were visualize by posterior pinhole imagery.

As seen by the data of Table 1, tumor localization was seen with $^{111}$In-labeled intact polyclonal IgG and its Fc fragment, but not with the F(ab')2 fragment. The biodistribution data revealed that about 32% of the injected dose of $^{111}$In-labeled Fc was retained per gram of tumor at 48 hours post-injection, which can be explained by the considerably higher blood activity in the IgG group (Table 1). The tumor-to-background ratio was 12:1 in the IgG group and 10:1 in the Fc group.

Imaging experiments were performed using $^{111}$In-labeled Fab and Fc modified' by cyclic anhydride-DTPA. In these experiments, tumor was detected with Fc fragments only.

It can be concluded that it is possible to detect Fc receptor-bearing tumors with non-specific polyclonal IgG in both its intact and Fc forms, but not in its F(ab)2 form. As tumor detection appears to depend on the presence of intact Fc fragments, it is likely to be mediated by the Fc receptor. In comparison with the biodistribution of F(ab')2 at 48 hours post-injection, there was no evidence that Fc fragment was significantly retained in tissues of the reticuloendothelial septem.

These data indicate that employment of Fc receptor imaging provides a new approach to early non-specific tumor detection.

TABLE 1

| | Biodistribution at 45 Hours | | | | | | | | | | | |
|---|---|---|---|---|---|---|---|---|---|---|---|---|
| | % Dose per Organ | | | | | | % Dose per g/Organ | | | | | |
| Organ | F(ab')$_2$ | ± S.D. | IgG | ± S.D. | Fc | ± S.D. | F(ab')$_2$ | ± S.D. | IgG | ± S.D. | Fc | ± S.D. |
| Blood | 0.31 | .09 | 18.7 | 3.7 | 2.46 | .48 | 0.17 | .01 | 8.64 | 1.5 | 1.27 | .34 |
| Heart | 0.10 | .01 | 0.28 | .08 | 0.1 | .01 | 0.7 | .13 | 1.86 | .5 | .56 | .13 |
| Liver | 4.59 | .4 | 13.54 | 1.11 | 4.41 | .24 | 2.93 | .43 | 9.07 | .34 | 3.2 | .43 |
| Kidneys | 3.5 | .7 | 3.97 | .81 | 10.65 | 4.64 | 8.57 | 1.4 | 10.58 | 1.37 | 32.78 | 11.5 |
| Lung | 0.19 | .09 | 0.55 | .05 | 0.13 | .02 | 0.75 | 0.3 | 2.79 | .52 | .96 | .2 |
| Spleen | 0.17 | .005 | 0.76 | .11 | 0.32 | .09 | 1.48 | .4 | 7.07 | 2.28 | 2.19 | .59 |
| Muscle | 2.29 | .39 | 11.42 | .33 | 6.89 | 2.69 | 0.22 | .04 | 0.95 | .09 | .64 | .29 |
| Bone | 2.14 | .58 | 7.27 | 2.6 | 3.16 | .75 | 0.77 | .2 | 2.21 | .02 | 1.13 | .39 |
| Tumor | | | 0.639 | .3 | 0.3 | .098 | | | 31.95 | 15.0 | 15.0 | 4.8 |

What is new and is desired to be covered by Letters Patent is:

1. A method of detecting an Fc receptor-expressing tumor site in vivo in an individual which comprises:
    administering to said individual a diagnostically effective amount of a non-specific detectably-labeled immunoglobulin or an Fc or Fc' fragment thereof;
    contacting said immunoglobulin or Fc or Fc' fragment thereof with Fc receptors at said tumor site; and
    detecting said detectably-labeled immunoglobulin or Fc or Fc' fragment thereof.

2. The method of claim 1, wherein said immunoglobulin is monoclonally derived.

3. The method of claim 1, wherein said immunoglobulin is polyclonally derived.

4. The method of claim 1, wherein said fragment is the Fc portion of said immunoglobulin.

5. The method of claim 1, wherein said fragment is the Fc' portion of said immunoglobulin.

6. The method as in any one of claims 1-5, wherein said detectable label is a radioactive isotope.

7. The method of claim 6, wherein said isotope is selected from the group consisting of $^{99m}$Tc, $^{123}$I, $^{131}$I, $^{111}$In, $^{97}$Ru, $^{67}$Cu, $^{67}$Ga, $^{68}$Ga, $^{72}$As, $^{89}$Zr, $^{201}$Tl or other positron emitter.

8. The method as in any one of claims 1-5, wherein said detectable label is a paramagnetic isotope.

9. The method of claim 8, wherein said paramagnetic isotope is selected from the group consisting of $^{157}$Gd, $^{55}$Mn, $^{162}$Dy, $^{52}$Cr, and $^{56}$Fe.

10. The method of claim 8, wherein said detecting is by magnetic resonance imaging or positron emission tomography.

11. The method of claim 1, wherein said administration is parenteral by bolus or infusion.

12. The method of claim 11, wherein said parenteral administration is by intradermal, subcutaneous, intramuscular, intraperitoneal, or intravenous injection.

13. The method as in any one of claim 1, wherein said individual is a human.

* * * * *